(12) United States Patent
Mäntylä

(10) Patent No.: US 7,588,643 B2
(45) Date of Patent: Sep. 15, 2009

(54) METHOD AND APPARATUS FOR MEASURING AMOUNT OF COATING ON PAPER WEB

(75) Inventor: Markku Mäntylä, Kangasala (FI)

(73) Assignee: Metso Automation OY, Helsinki (FI)

(*) Notice: Subject to any disclaimer, the term of this patent is extended or adjusted under 35 U.S.C. 154(b) by 264 days.

(21) Appl. No.: 10/509,878

(22) PCT Filed: Apr. 15, 2003

(86) PCT No.: PCT/FI03/00297

§ 371 (c)(1), (2), (4) Date: Dec. 3, 2004

(87) PCT Pub. No.: WO03/087814

PCT Pub. Date: Oct. 23, 2003

(65) Prior Publication Data

US 2005/0106312 A1   May 19, 2005

(30) Foreign Application Priority Data

Apr. 16, 2002   (FI) .................................. 20020732

(51) Int. Cl.
B05C 11/10   (2006.01)
(52) U.S. Cl. .................. 118/665; 118/690; 118/691; 118/689; 118/688; 162/112; 162/119; 162/135; 162/136; 162/137

(58) Field of Classification Search .................. 118/664, 118/665, 688, 689, 690, 691, 713; 162/112, 162/119, 135, 136, 137, 265
See application file for complete search history.

(56) References Cited

U.S. PATENT DOCUMENTS

| | | | |
|---|---|---|---|
| 6,183,561 B1 * | 2/2001 | Belotserkovsky | 118/665 |
| 6,248,174 B1 * | 6/2001 | Kustermann | 118/665 |
| 6,452,679 B1 * | 9/2002 | Workman, Jr. | 356/429 |
| 6,521,089 B1 * | 2/2003 | Griech et al. | 162/198 |

FOREIGN PATENT DOCUMENTS

| | | |
|---|---|---|
| SU | 1679374 A1 | 9/1991 |
| WO | WO 01/36949 A1 | 5/2001 |
| WO | WO 01/50112 A1 | 7/2001 |

* cited by examiner

Primary Examiner—George R Koch, III
(74) Attorney, Agent, or Firm—Oliff & Berridge, PLC

(57) ABSTRACT

A method and an apparatus for measuring the amount (CW) of a coating (2) on a paper web (1). The amount (CA) of at least one component in the coating (2) on the paper web (1) is measured and the composition (CC) of the coating (2) to be transferred to the paper web (1) is determined. The amount (CW) of the coating (2) on the paper web (1) is determined on the basis of the amount (CA) of at least one component in the coating (2) on the paper web (1) and the composition (CC) of the coating (2) to be transferred to the paper web (1).

16 Claims, 3 Drawing Sheets

METHOD AND APPARATUS FOR MEASURING AMOUNT OF COATING ON PAPER WEB

This application is a national stage entry of PCT/FI03/00297, filed on Apr. 15, 2003.

FIELD OF THE INVENTION

The invention relates to a method of measuring the amount of a coating on a paper web, in which method the amount of at least one component of the coating on the paper web is measured.

The invention also relates to an apparatus for measuring the amount of a coating on a paper web.

BACKGROUND OF THE INVENTION

Paper coating refers to its coating with various substances, the mostly used being pigment-containing coating colours. Other generally used coatings include waxes, plastics, silicone, surface sizes and starch. The purpose of coating is to fill the irregularities on the paper surface with one or more coating layers. Coating primarily affects the printability and appearance of paper, but also the stiffness of paper and its resistance to water, grease or solvents.

A coating is composed of an aqueous solution of one or more pigments, one or more binders, and additives. For some special papers, solvent-based coatings are used. Accordingly, pigments, binders and additives constitute the components of a coating. A coating is prepared at a coating kitchen by mixing these components. The mixing can be performed either in doses as batch production or by continuous mixing. The proportions or amounts of the different components are given in colour formulas. From the coating kitchen, the coating is transferred to a coating head, where it is evenly applied onto the surface of a paper web. The thickness, i.e. amount ($g/m^2$) of the coating layer is adjusted suitable by peeling excess coating off the paper by means of a doctor blade. The amount of the coating is adjusted by changing the position of the doctor blade relative to the paper web. Excess coating is directed to a circulation, from where it is reapplied onto the surface of the paper. The coating layer remaining on the surface of the paper is dried by evaporating the excess water contained by the coating with coating drying units located after the coating head. Either both or only one side of the paper can be coated by using either separate coating heads or by coating both sides simultaneously. The coatings on the different sides of the paper may also be identical or different depending on the unequal sidedness of the base or the operational asymmetry required by the end product.

For adjustment of the amount of a coating on the paper, the amount of the coating remaining on the paper is measured and, based on said measurement, the position of the doctor blade is changed relative to the paper web, if required, to change the amount of the coating. Nowadays, the amount of a paper coating is measured by IR measurement. U.S. publication 4,957,770 discloses a method based on IR measurement for sensing the amount of a coating on a moving base. Measuring the amount of a coating by IR measurement is based on a measurement of the ratio of the reflection intensities of the IR absorption wavelength bands and reference wavelength bands characteristic of the different components of the coating and water and fibres. The ratio of the reflection intensities of the absorption wavelength bands and the reference wavelength bands corresponding to the components enables the determination of the amount of each component in the coating remaining in the paper. The total amount of coating remaining in the paper can be determined based on the amount of a component, once the formula of the coating applied onto the paper, i.e. the substances mixed into the coating and the amounts thereof are known.

However, a problem in present solutions for measuring the amount of a coating is that the composition of the coating has to correspond to the formula exactly in order for the amount of the coating remaining in the paper to be determined correctly. Because of the recycling of coating or problems associated with its manufacture, the composition of the coating may change, i.e. the coating no longer corresponds to the formula. When the coating does not correspond to the formula, the total amount of the coating in the paper cannot be determined exactly. In batch processes, the composition of the coating may differ from what is stated in the formula for instance because of inaccuracy in metering the components of the coating, transition points occurring in grade changes or incomplete washing of coating treatment devices. In a continuous coating production process, inaccuracy is caused for instance by inaccuracy in metering measurements, unfamiliarity of recycled pigments precipitated in washing and grade changes.

BRIEF DESCRIPTION OF THE INVENTION

The object of the present invention is to provide a new type of method and apparatus for measuring the amount of a paper coating.

The method of the invention is characterized by determining the composition of the coating to be transferred to the paper web, and determining the amount of the coating on the paper web on the basis of the amount of at least one component of the coating on the paper web and the composition of the coating to be transferred to the paper web.

The apparatus of the invention is characterized in that the apparatus comprises a first measuring device arranged to measure the amount of at least one component in the coating on the paper web by reflection measurement, a second measuring device arranged to determine the composition of the coating to be transferred to the paper web, and a data processing device arranged to determine the amount of the coating on the paper web on the basis of the amount of at least one component of the coating on the paper web and the composition of the coating to be transferred to the paper web.

The essential idea of the invention is to measure the amount of a coating on a paper web by measuring the amount of at least one component of the coating on the paper web, by determining the composition of the coating to be transferred to the paper web and by determining the amount of the coating on the paper web on the basis of the amount of at least one component of the coating and the composition of the coating of the paper web to be transferred to the paper web. According to an embodiment of the invention, the amount of at least one component of the coating on the paper web is measured by reflection measurement based on infrared technique. According to a second embodiment of the invention, the composition of the coating to be transferred to the paper web is determined by reflection measurement based on infrared technique. According to a third embodiment of the invention, the composition of the coating to be transferred onto the paper web is determined by Raman spectroscopy based on molecular vibration spectroscopy. According to a fourth embodiment of the invention, the amount of at least one component of the coating to be measured is the amount of a pigment in the coating on the paper web. According to a fifth embodiment of the invention, the amount of the coating on the paper web is adjusted on the basis of a measurement of the amount of the coating on said paper web.

An advantage of the invention is that the exact amount of a paper coating is found out in all running conditions, and a deviation in the composition of the coating from the formula does not cause an error in the measurement of the amount of the coating. The formula used in the preparation of the coating does not have to be known, and grade changes do not either cause problems in measuring the amount of the coating. When the composition of the coating to be transferred to the paper web is determined by reflection measurement based on infrared technique or by Raman spectroscopy based on molecular vibration spectroscopy, the composition of the coating can be determined rapidly during normal process operation without laboratory analyses causing long delays. When the composition of the coating is determined by Raman spectroscopy, the composition of aqueous samples can also be measured extremely accurately, since water is a weak Raman scatterer. The amount of at least one component to be measured of the coating on the paper web is preferably the amount of a pigment in the coating, since the proportion of pigments in the dry matter of the coating is typically the highest. An exact measurement of the amount of the coating on a paper web further enables an accurate adjustment of the amount of the coating on the paper web.

In the context of the present description, the term 'paper' refers to both paper and paperboard.

BRIEF DESCRIPTION OF THE FIGURES

The invention will be described in detail in the attached drawings, wherein.

DETAILED DESCRIPTION OF THE INVENTION

Figure 1:
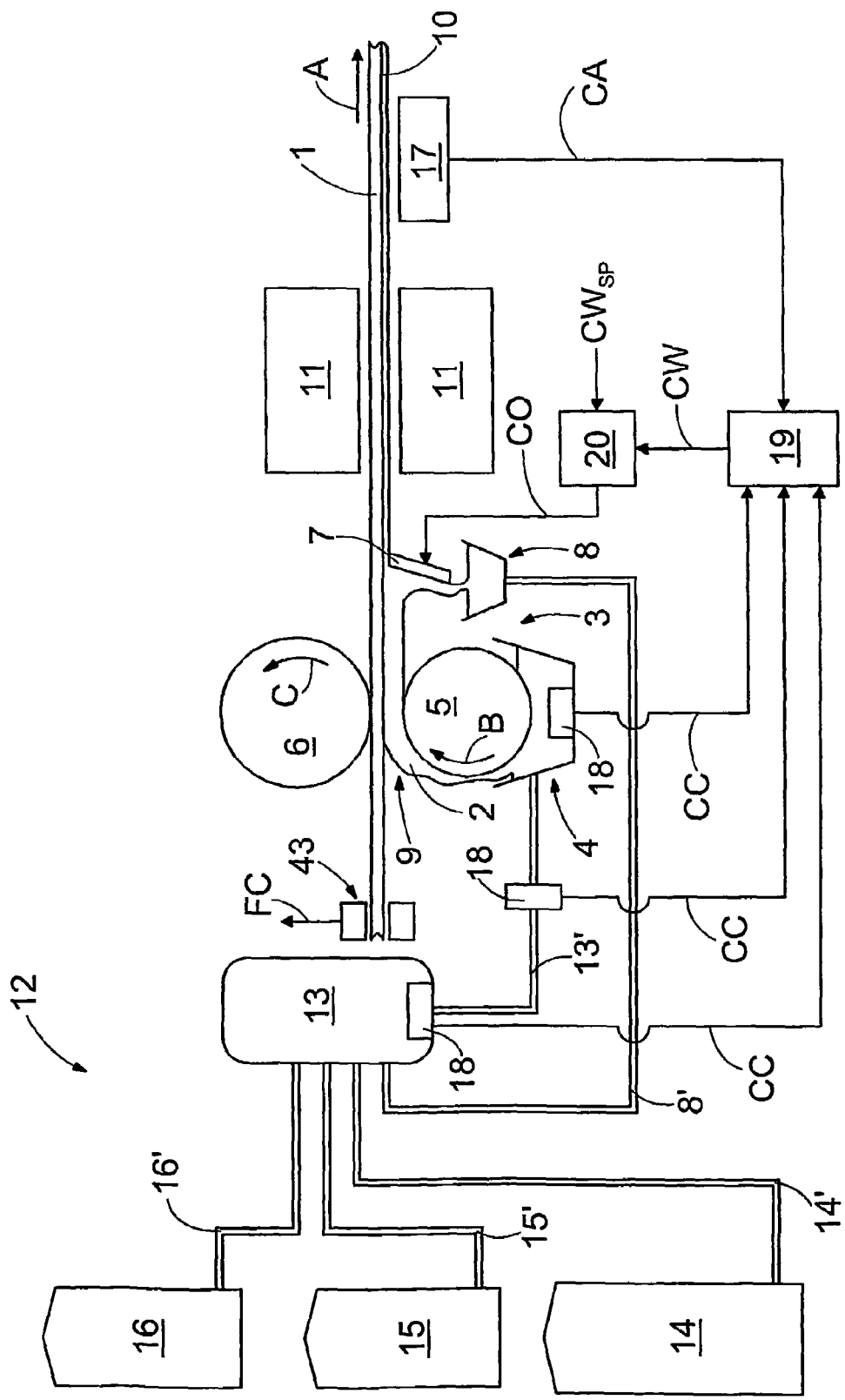
FIG. 1 schematically shows a paper coating process and an apparatus for measuring the amount of a paper coating, FIG. 2 schematically shows a measuring device for measuring the amount of at least one component of a coating on a paper web, FIG. 3 schematically shows a measuring result of the measuring device according to FIG. 2, FIG. 4 schematically shows a measuring device for determining the composition of a coating to be transferred to a paper web, and FIG. 5 schematically shows a measuring result of the measuring device according to FIG. 4.

FIG. 1 schematically shows a coating process for coating a paper web 1 moving in the direction of arrow A with a coating 2 or coating colour 2. Various pigment-containing coating colours or waxes, plastics, silicone, surface sizes or starch can be used as the coating 2. The coating process includes a coating head 3, by means of which the coating 2 is conveyed, i.e. applied to the lower surface of the paper web 1. The coating head 3 includes a coating colour reservoir 4 or applicator pan 4, an applicator roll 5, a backing roll 6, a doctor blade 7 or blade 7 and a collector pan 8. The coating head 3 shown in FIG. 1 is a roll applicator or roll coater, wherein the coating 2 is lifted in the coating colour reservoir 4 to the lower surface of the paper web 1 supported by the backing roll 6 by means of the applicator roll 5 rotating in the direction of arrow B. The backing roll 6 naturally rotates in the direction shown by arrow C. The amount of a coating 2 conveyed by the applicator roll 5 to the surface of the paper web 1 is affected by the size of an application gap 9 or nip 9 between the applicator roll 5 and the backing roll 6, the properties of the coating 2, the speed of the applicator roll 5, and the diameter and hardness of the applicator roll 5 and the backing roll 6. The amount of coating transferred from the coating colour reservoir 4 to the paper web 1 is typically about 200 to 250 g/m². After the coating 2 is applied, the coating 2 is levelled or metered with the doctor blade 7, whereby excess coating 2 is collected to the collector pan 8, from where it can again be recycled for reuse. After the levelling, the amount of coating remaining in the paper web 1 varies between 0.5 and 50 g/m². After the levelling of the coating, a coating layer 10 remaining in the paper web 1 is dried by removing the excess water conveyed to the web together with the coating 2 using drying units 11 intended for drying the coating. For the sake of clarity, FIG. 1 shows the paper web 1 and the coating layer 10 remaining on top of it substantially thicker than they really are as compared with the structure of the coating process.

The coating process of FIG. 1 further comprises a coating preparation process 12 for preparing the coating 2. The coating 2 is typically composed of an aqueous solution of one or more pigments, one or more binders, and additives, but in association with some special papers, solvent-based coatings are used. The coating preparation process 12 shown in FIG. 1 is a continuous process including a mixer 13, wherein a pigment conveyed along a transfer line 14' from a pigment tank 14, a binder conveyed along a transfer line 15' from a binder tank 15, an additive conveyed along a transfer line 16' from an additive tank 16, and the excess coating returning along a recycling line 8' from the collector pan 8 of the coating head 3, are mixed together. The finished coating is conveyed from the mixer 13 along a feed line 13' to the coating colour reservoir 4. Pigments and additives are stored in the pigment 14 and binder 15 tanks as slurries mixed in water. For the sake of clarity, FIG. 1 only shows one pigment tank 14, binder tank 15 and additive tank 16, but it is apparent that the different pigments, binders and additives are stored each in a separate tank. The recycling line 8' also comprises different devices used for purifying the recycled coating, but they are not shown for the sake of clarity. Further, for the sake of clarity, FIG. 1 does not show the pumps and valves required in the transfer, recycling and feed lines for transfer and guidance of both the finished coating and the different components of the coating.

The pigments most generally used include kaolin and calcium carbonate. Other generally used pigments include talc, gypsum, titanium dioxide, aluminium hydroxide, and calcinated kaolin. The portion of pigment in the dry matter content of the coating 2 is typically between 70 and 95%, and thus it mainly determines the quality and properties of the coating 2. The binder serves to bind the pigment particles to each other and to the paper web 1. Natural binders include starch, soybean protein and casein. Synthetic additives include for instance different latexes, such as styrene butadiene (SB) latex, and carboxy-methyl cellulose (CMC). The portion of binders in the dry matter content of the coating is usually between 5 and 25%. Additives are used to adjust different properties of the coating, such as viscosity and water retention. Urea or polyethylene glycol, for example, can be used to lower the viscosity of the coating. The water retention of the coating can be adjusted with CMC or starch, for example. Other additives used in coatings include for instance antifoam agents and foam inhibitors, lubricants, hardeners and optical clarifying agents. The portions or amounts of components to be mixed in the coating are given in formulas, wherein the amounts of components are given by denoting the total dry matter amount of the different pigments by the ratio 100, the portions of the different pigments being given as dry matter portions. The amounts of binders and additives are given as the portion of their dry matter in the total dry matter of the pigments. The ratios of the different components of the coating vary depending on the grade and purpose of use of the paper, and the coating method.

Paper coating and preparing a coating are known per se to a person skilled in the art, and they are thus not described in detail herein. It is thus apparent that the operating principle of the coating head used to coat paper may vary, i.e. instead of roll application, for instance short dwell application or nozzle application can be used, whereby the amount of the coating transferred to the paper web 1 at the coating head may vary significantly. Furthermore, the coating may be prepared as batch production instead of continuous preparation, whereby the coating is transferred from the coating kitchen to a storage tank and from there to a machine tank, from where the coating is pumped to the coating colour reservoir of the coating head.

For measuring the amount CW of a coating in the paper web 1, i.e. the total amount CW of the coating remaining in the paper web 1 after levelling, a first measuring device 17 is used to measure the amount CA of at least one component in the coating remaining in the paper web 1 after the levelling of the coating, and a second measuring device 18 is used to determine the composition CC of the coating to be transferred to the paper web 1, i.e. the different components of the coating and their amounts or portions relative to each other. The amount CW of the coating in the paper web 1 is found out by combining the amount of at least one component in the coating measured with the first measuring device 17 and the composition of the coating determined with the second measuring device 18.

The measurement of the amount of a coating in the paper web 1 on the basis of said measurements can be illustrated by an example, wherein the first measuring device 17 is arranged to measure the amount of calcium carbonate, the measuring result being 5 g/m². The second measuring device 18 was used to determine the composition of the coating, according to which the portion of calcium carbonate in the coating to be applied to the paper web 1 is 60% of the total amount of the pigments. Accordingly, in accordance with the above description, the ratio of calcium carbonate is 0.6. Furthermore, the total ratio of the pigments, binders and additives contained by the coating, obtained on the basis of the composition of the coating measured with the second measuring device 18 is 1.15. These values are used to calculate the amount CW of the paper coating using the formula $$CW = \frac{5 \text{ g/m}^2}{0.6} \times 1.15 = 9.6 \text{ g/m}^2. \quad (1)$$

The amount CA of at least one component in the coating measured with the first measuring device 17 is combined with the composition CC of the coating determined with the second measuring device 18 in a data processing device 19, which is for instance a microprocessor-based or signal processor-based device, which uses software to determine the amount CW of the paper coating. Instead of the data processing device 19 determining the amount CW of the paper coating on the basis of the amount CA of at least one component in the coating and the composition CC of the coating given directly by the measuring devices 17 and 18, the data processing device 19 can be arranged to determine said quantities on the basis of other measuring results obtained from the measuring devices 17 and 18 and indirectly descriptive of said quantities.

The first measuring device 17 is arranged to measure the amount CA of at least one component in the coating remaining in the paper using a reflection measurement method based on the IR (infrared) technique. The first measuring device 17 is arranged after the coating drying units 11. If the coating head 3 is directly integrated into a paper machine, then the first measuring device 17 is typically arranged in a measuring carriage moving in a measuring frame immediately before the reeler of the paper machine, the sledge moving transversely to the paper web 1 perpendicularly across the paper web 1 to and fro as the paper web 1 continuously moves forward. The second measuring device 18 is arranged to determine the composition CC of the coating to be applied to the paper web 1 either as the first measuring device 17, using reflection measurement based on IR technique or the CCD Raman technique. The second measuring device 18 can be arranged in several points of the coating process. FIG. 1 shows some potential points where the second measuring device 18 can be arranged. These points include the mixer 13, the coating colour reservoir 4, and the feed line 13' between them. In batch production of coating, the second measuring device 18 can be arranged in the coating colour reservoir, in the storage or machine tank of the finished coating or in the transfer line between them, or in the feed line between the machine tank and the coating colour reservoir. It is also possible to arrange the second measuring device 18 by providing a separate sample line for the second measuring device 18 for instance in one of the aforementioned tanks or the coating colour reservoir.

By determining the composition CC of the coating to be applied to the paper and by comparing the amount CA of at least one component in the coating, measured from the paper, with said composition CC of the coating, the exact amount CW of the coating in the paper is found out in all running conditions. The formula used in the preparation of the coating does not have to be known, and any disturbances in the production of the coating resulting in a deviation in the composition of the coating do not affect the measurement of the amount CW of the coating according to the solution. Paper grade or grade change, in association with which the composition of the coating may change, does not either affect the measurement of the amount CW of the coating.

In some cases, the same material, e.g. calcium carbonate or kaolin, is used as filler in the paper to be coated as is used as a component in the coating. In these cases, the same component contained by the paper may disturb the measurement of the amount of the coating. In this case it is appropriate to measure the amount of the same component contained by the paper before the paper is coated and correct the result obtained from the coated paper according to the measurement of the uncoated paper, i.e. the base. FIG. 1 schematically shows a third measuring device 43, arranged to measure the amount FC of a corresponding filler contained by the paper before the paper is coated using for instance through-measurement, methods based on the absorption of radiation, known per se to a person skilled in the art.

Figure 2:
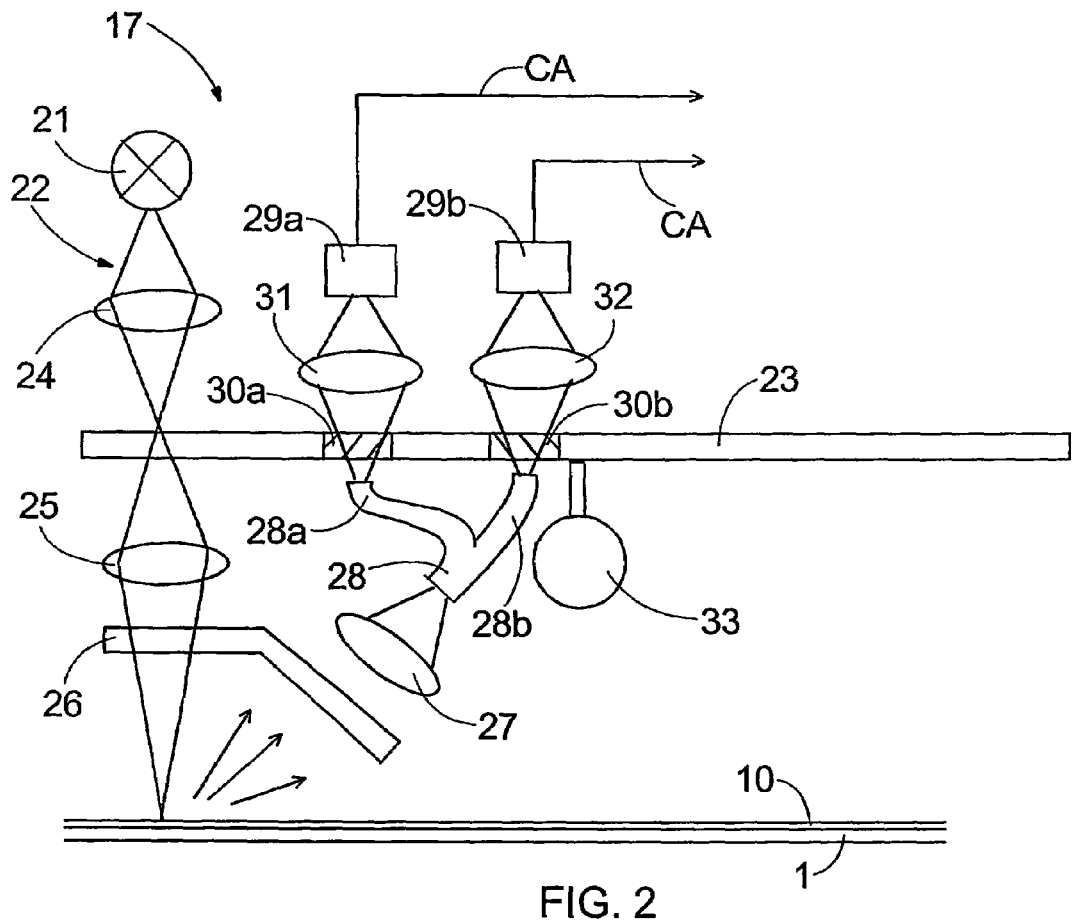

FIG. 2 schematically shows a first measuring device 17, which can be used to measure the amount CA of at least one component of the coating in the paper. The operation of the measuring device 17 is based on reflection measurement at IR wavelengths, the measuring device transmitting infrared radiation to the object measured and measuring the radiation reflected from the object. The radiation source and the receiver are thus arranged on the same side of the object to be measured. The operation of the first measuring device 17 is based on the measurement of the ratio of the reflection intensities of the IR absorption wavelength bands and reference wavelength bands characteristic of the different components of the coating and water and fibres. The ratio of the reflection intensities of the absorption wavelength bands and reference wavelength bands corresponding to each component can be used to determine the amount of each component in the coating remaining in the paper.

The first measuring device 17 according to FIG. 2 comprises a radiation source 21 that generates a beam of light 22. The radiation source 21 may be for instance a halogen lamp or another suitable radiation source for generating an infrared beam. The beam of light 22 is directed with a first lens 24 to a chopper 23. Instead of the first lens 24, a lens combination or a concave mirror can be used, which directs the beam of light 22 transmitted by the radiation source 21 to the chopper 23. The beam of light 22 directed to the chopper 23 is directed further using a second lens 25 to the object to be measured, i.e. the paper web 1 or a paperboard web and to a coating layer 10 therein. In this case, too, a lens combination or a concave mirror can be used instead of the second lens 25. The chopper 23 serves to chop the optical radiation transmitted by the radiation source 21 into light pulses so that part of the time the chopper 23 lets through optical radiation and part of the time the chopper 23 prevents the radiation from getting through it. An essential feature of the operation of the chopper 23 is thus that the object measured is illuminated during the illumination time using IR radiation emitted from the radiation source 21, and during the illumination blocking time, the object measured is not illuminated with the IR radiation emitted from the radiation source. The chopper 23 is preferably a rotating disk, rotated by an electric motor 33. Between the second lens 25 and the object measured, a cover 26 can be used, which is of plastic, glass, or other material that permeates the IR radiation to be measured and which serves to protect the imaging optics particularly under industrial circumstances, i.e. the first lens 24, the second lens 25, the chopper 23 and the radiation source 21 from being fouled.

The optical radiation emitted by reflection or scattering from the object to be measured is collected with a third lens 27, and focused for instance to an optical fibre or a fibre bundle 28. Furthermore, the cover 26 may also be extended between the object measured and the third lens to prevent the side receiving the optical radiation from being fouled, particularly under industrial circumstances. From the fibre or the fibre bundle 28, the optical radiation moves towards filtering and detectors 29a and 29b. Since the measuring device shown by FIG. 2 comprises two detectors 29a and 29b, the fibre bundle 28 is divided into two branches 28a and 28b. The radiation emitted from branch 28a is filtered with a MIR filter (Middle IR) 30a arranged in association with the chopper 23, and the radiation emitted from branch 28b is simultaneously filtered with a NIR filter (Near IR) 30b. The filters filter the light such that only the light essential to the measurement and in the right wavelength range reaches the detectors. The filtered MIR radiation is focused with a fourth lens 31 to the first detector 29a and the filtered NIR radiation is focused with a fifth lens 32 to the second detector 29b. The chopper 23 comprises at least two MIR filters 30a, the first MIR filter letting through a wavelength range sensitive to the coating component to be measured, the second MIR filter letting through a wavelength range sensitive both to the base, i.e. the uncoated paper web 1, and the coating component to be measured. The chopper similarly comprises at least two NIR filters 30b. From the detectors 29a and 29b, the measured signals are led either to a data processing unit inside the first measuring device 17 or to the data processing device 19 shown in FIG. 1 for determining the amount CA of the component to be measured in a manner known per se to a person skilled in the art.

The measuring device shown in FIG. 2 can be used for simultaneous measurement of at least two different components of the coating. In the MIR range, typically referring to the electromagnetic spectral band 2500 nm to 20000 nm, the amount of for instance calcium carbonate, kaolin, silicone or water can be measured. In the NIR range, typically referring to the electromagnetic spectral band 700 nm to 2500 nm, the amount of for instance kaolin, talc, gypsum, latex, starch, silicone or water can be measured. The measurement of water can be used to determine the moisture content and further specify the measurement of the amounts of the other components. When several MIR and NIR filters at different wavelength ranges are arranged in the chopper 23, the same measuring device can be used to substantially simultaneously measure more than two coating components. Furthermore, the first measuring device 17 shown in FIG. 2 is only one feasible measuring device for measuring the amount CA of at least one coating component, and thus very many different measuring devices can be used to measure the amount CA of at least one component of the coating.

Figure 3:
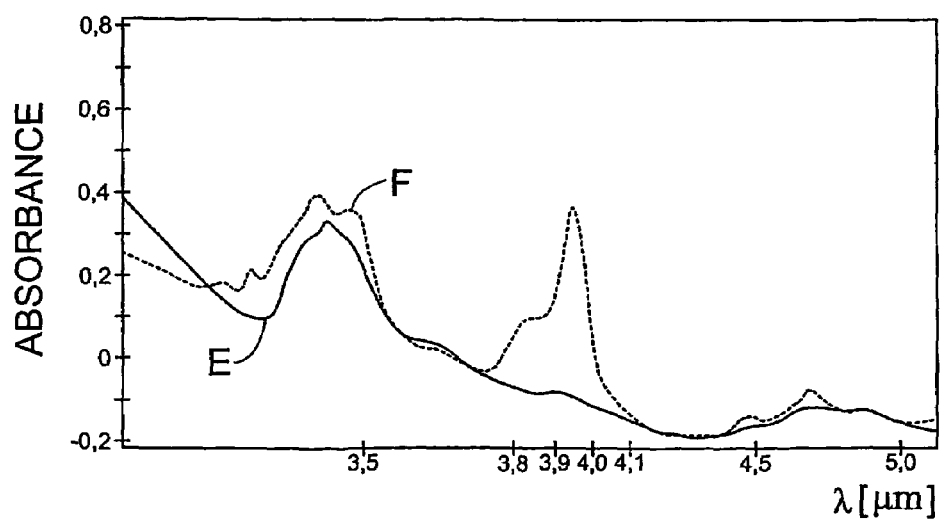

FIG. 3 schematically shows by way of example a measurement performed with the first measuring device 17 according to FIG. 2, wherein the reflection spectrum of the stock or base paper constituting the measuring base, i.e. the uncoated paper web 1, is shown by curve E, drawn by a continuous line, and the reflection spectrum of paper coated with a coating containing calcium carbonate by curve F, drawn by a broken line. The horizontal axis shows wavelength $\lambda$ in micrometers ($\mu$m) and the vertical axis the absorbance of the beam of light 22. Curve F shows the absorption peak of calcium carbonate at a wavelength of approximately 3.95 micrometers. Reference wavelengths suitable for measuring calcium carbonate are 4.55 micrometers and/or 3.7 micrometers, for example. Any reference wavelengths close to the actual measuring peak are usable as reference wavelengths. It is essential that the absorbance of the stock and the coated paper in said reference wavelength range is the same or approximately the same. A wavelength of 3.7 micrometers is particularly advantageous, since it can be used as reference also in the measurement of the amount of water. The amount of water is preferably measured at a wavelength of about 3.175 micrometers, for example. The measurement of the amount of water can be used to compensate for the effect of the water in the coating and the paper in the measurement of the amount of the coating. The amount of a pigment in the coating is preferably used as the amount of the coating component to be measured, since their portion in the coating is typically highest.

Figure 4:
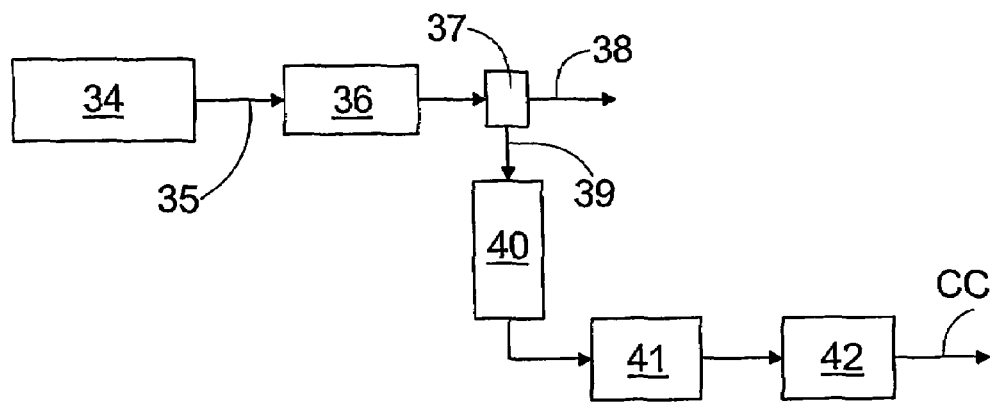

FIG. 4 schematically shows a second measuring device 18 usable for determining the composition CC of a coating to be transferred to paper. The second measuring device 18 shown in FIG. 4 is a Raman spectrometer operating by Raman spectroscopy based on molecular vibration spectroscopy. Raman spectroscopy is a method supporting IR spectroscopy, its advantages compared with the IR technique being less need for sample processing, since Raman spectroscopy can be used for direct measurement of powdery, liquid or solid samples. A further advantage is the rapidity of the measurement and the ability to measure aqueous samples, since water is a weak Raman scatterer. A still further advantage of the Raman technique compared with the IR technique is simple calibration, which can be implemented as the ratio of the areas of two intensity peaks of the Raman spectrum.

The Raman spectrometer shown in FIG. 4 comprises a laser 34, a monochromatic illumination 35 transmitted by which is focused by imaging optics 36 to a sample 37 to be analyzed. Lenses or fibre optical measuring heads or combinations thereof, for example, are usable as the imaging optics 36. Part of the monochromatic illumination 35 transmitted by the laser 34 passes through the sample 37. Arrow 38 denotes this part of the illumination 35 transmitted by the laser 34. The rest of the monochromatic illumination 35 transmitted by the laser 34 is scattered from the sample 37. Light, denoted by arrow 39 and scattered from the sample 37 and containing information about the molecular vibration in the sample caused by the light transmitted by the laser 34, is collected by measuring optics 40. Lenses or fibre optical measuring heads or combinations thereof, for example, are usable as the measuring optics 40. The measuring optics 40 leads the light scattered from the sample 37 to a detector 41, to which the Raman spectrum descriptive of the composition CC of the sample 37 is imaged or recorded. A CCD camera, for example, can be used as the detector 41. The Raman spectrometer of FIG. 4 further comprises a data processing unit 42 for determining the composition CC of the sample 37 on the basis of the Raman spectrum imaged in the detector. Instead of the data processing unit 42, the data processing unit 19 shown in FIG. 1 can also be used to determine the composition CC of the sample 37. FIG. 4 schematically shows only one feasible embodiment of a Raman spectrometer. Raman spectroscopy and different Raman spectrometers are known per se to a person skilled in the art and are therefore not described in detail herein.

Figure 5:
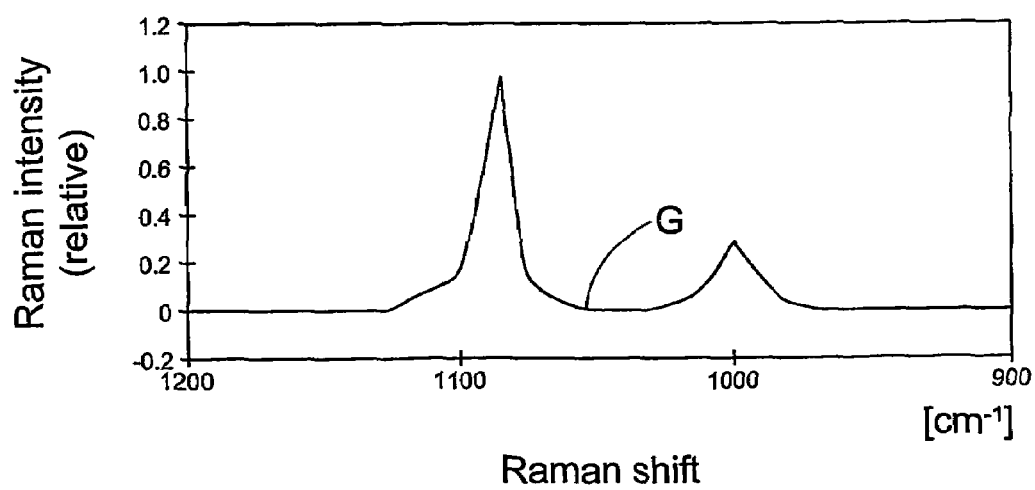

FIG. 5 schematically shows, on curve G, by way of example a measurement of the composition CC of the coating performed with the second measuring device 18 of FIG. 4, a basic level correction being performed on curve G. The horizontal axis shows the magnitude of the Raman shift in $cm^{-1}$ and the vertical axis the Raman intensity proportioned to the largest peak. Said peaks denote the amounts and ratios of the components contained by the coating to be transferred to the paper. At about 1082 $cm^{-1}$ in the Raman shift, curve G shows a calcium carbonate peak, and at about 1002 $cm^{-1}$ in the Raman shift a SB latex peak. Should the coating include other components, their peaks would be shown at such points in the Raman shift that are characteristic of them. A comparison of the height and/or areas of the peaks with the basic level of the Raman spectrum enables the calculation of the ratio of the different components contained in the coating and/or the amount of one or more components. The determined composition CC of the coating is used in the above-described manner for measuring the amount CW of coating applied onto the paper.

Instead of a Raman spectrometer and Raman spectroscopy, measuring devices based on the IR technique can also be used for determining the composition CC of the coating to be transferred to the paper, but the composition of the coating is preferably determined by Raman spectroscopy.

Accurate measurement of the amount of the coating CW in the paper web 1 under papermaking enables accurate adjustment of the amount CW of the coating in the paper web 1. In a coating head 3 according to FIG. 1, the amount CW of the coating is adjusted by changing the position of the doctor blade 7 relative to the paper web 1. The position of the doctor blade 7 is changed by controlling the operation of the actuator affecting the doctor blade 7 in accordance with a control variable CO obtained from a control device 20 shown in FIG. 1. The control variable CO is determined on the basis of the difference between the amount CW of the coating measured in the control device 20 and the set value $CW_{SP}$ descriptive of the target value of the amount CW of the coating. Although FIG. 1 shows the control device 20 as a device separate from the data processing device 19, it is naturally clear that the operations of the control device 20 can also be implemented in the data processing device 19.

The drawings and the related specification are only intended to illustrate the inventive idea. The details of the invention may vary within the scope of the claims. It is thus clear that when both sides of the paper web 1 are coated, the amount of the coating on both sides of the paper web 1 can be measured using a similar arrangement. If both sides are coated with the same coating, the composition CC of the coating determined by the same second measuring device 18 can be used in measuring the amount CW of the coating on both sides. Furthermore, the solution presented is preferably used for continuous measurement of the amount of the coating in the paper, i.e. when the previous measuring result is obtained, the measurement is immediately or substantially immediately restarted. If the operation of the coating head is very stable, it is sufficient to measure the amount of the coating only randomly or at preset intervals. The solution presented is naturally usable in coating paper during papermaking or in coating finished paper in a coating device separate from the paper machine.

The invention claimed is:

1. A method of measuring an amount of a coating on a paper web, the method comprising:
   measuring an amount of at least one component of the coating on the paper web;
   measuring a chemical composition of a coating to be transferred to the paper web by determining at least one of an amount of at least one component in the coating to be transferred to the paper web and a ratio of two or more components in the coating to be transferred to the paper web; and
   determining an amount of the coating on the paper web on a basis of the amount of the at least one component of the coating on the paper web and the measured chemical composition of the coating to be transferred to the paper web,
   wherein the amount of the at least one component of the coating on the paper web is measured by a reflection measurement based on an infrared technique.

2. The method as claimed in claim 1, further comprising adjusting the amount of the coating on the paper web on a basis of the measurement of the amount of the coating on the paper web.

3. The method as claimed in claim 1, wherein the chemical composition of the coating to be transferred to the paper web is determined by a reflection measurement based on an infrared technique.

4. The method as claimed in claim 1, wherein the chemical composition of the coating to be transferred to the paper web is determined by a Raman spectroscopy based on a molecular vibration spectroscopy.

5. The method as claimed in claim 1, wherein the amount of the at least one component of the coating on the paper web is measured continuously.

6. The method as claimed in claim 1, wherein the amount of the at least one component of the coating on the paper web is an amount of a pigment in the coating on the paper web.

7. The method as claimed in claim 1, wherein the chemical composition of the coating to be transferred to the paper web is determined continuously.

8. An apparatus for measuring an amount of a coating on a paper web, the apparatus comprising:
   a first measuring device arranged to measure an amount of at least one component in the coating on the paper web by reflection measurement;

a second measuring device arranged to measure a chemical composition of a coating to be transferred to the paper web, the chemical composition being at least one of an amount of at least one component in the coating to be transferred to the paper web and a ratio of two or more components in the coating to be transferred to the paper web; and a data processing device arranged to determine the amount of the coating on the paper web on a basis of the amount of the at least one component of the coating on the paper web and the measured chemical composition of the coating to be transferred to the paper web, wherein the first measuring device is arranged to measure the amount of the at least one component of the coating on the paper web by a reflection measurement based on an infrared technique.

9. The apparatus as claimed in claim 8, the apparatus further comprising a control device arranged to adjust the amount of the coating on the paper web on a basis of the measurement of the amount of the coating on the paper web.

10. The apparatus as claimed in claim 8, wherein the second measuring device is arranged to determine the chemical composition of the coating to be transferred to the paper web by a reflection measurement based on an infrared technique.

11. The apparatus as claimed in claim 8, wherein the second measuring device is arranged to determine the chemical composition of the coating to be transferred to the paper web by a Raman spectroscopy based on a molecular vibration spectroscopy.

12. The apparatus as claimed in claim 8, wherein the first measuring device is arranged to measure the amount of the at least one component of the coating on the paper web continuously.

13. The apparatus as claimed in claim 8, wherein the amount of the at least one component of the coating on the paper web is an amount of a pigment in the coating on the paper web.

14. The apparatus as claimed in claim 8, wherein the second measuring device is arranged to determine the chemical composition of the coating to be transferred to the paper web continuously.

15. The apparatus as claimed in claim 8, wherein the second measuring device is arranged in a coating colour reservoir in a coating head, in a coating mixer, in a feed line between the coating mixer and the coating colour reservoir or in a separate sample line leaving the coating colour reservoir.

16. The apparatus as claimed in claim 8, wherein the second measuring device is arranged in a coating colour reservoir in a coating head, in a coating storage or a machine tank, in a transfer line between the coating storage and the machine tank, in a transfer line between the machine tank and the coating colour reservoir, in a separate sample line leaving the coating storage or the machine tank or in a separate sample line leaving the coating colour reservoir.

* * * * *